(12) United States Patent
Schouenborg

(10) Patent No.: US 11,969,589 B2
(45) Date of Patent: Apr. 30, 2024

(54) POSITIONAL STABILIZATION OF TISSUE-IMPLANTED MEDICAL DEVICES

(71) Applicant: NEURONANO AB, Karlshamn (SE)

(72) Inventor: Jens Schouenborg, Lund (SE)

(73) Assignee: NEURONANO AB (SE)

( * ) Notice: Subject to any disclaimer, the term of this patent is extended or adjusted under 35 U.S.C. 154(b) by 552 days.

(21) Appl. No.: 16/762,531

(22) PCT Filed: Nov. 6, 2018

(86) PCT No.: PCT/SE2018/000031
§ 371 (c)(1),
(2) Date: May 8, 2020

(87) PCT Pub. No.: WO2019/093936
PCT Pub. Date: May 16, 2019

(65) Prior Publication Data
US 2020/0346002 A1    Nov. 5, 2020

(30) Foreign Application Priority Data

Nov. 9, 2017 (SE) .................................. 1700274-2

(51) Int. Cl.
| | |
|---|---|
| A61N 1/05 | (2006.01) |
| A61L 31/02 | (2006.01) |
| A61L 31/04 | (2006.01) |
| A61L 31/10 | (2006.01) |
| A61L 31/12 | (2006.01) |
| A61L 31/14 | (2006.01) |

(52) U.S. Cl.
CPC .......... *A61N 1/0529* (2013.01); *A61L 31/022* (2013.01); *A61L 31/042* (2013.01); *A61L 31/045* (2013.01); *A61L 31/10* (2013.01); *A61L 31/125* (2013.01); *A61L 31/148* (2013.01); *A61N 1/05* (2013.01); *A61L 2420/04* (2013.01)

(58) Field of Classification Search
None
See application file for complete search history.

(56) References Cited

U.S. PATENT DOCUMENTS

| | | | |
|---|---|---|---|
| 7,949,412 B1 | 5/2011 | Harrison et al. | 607/137 |
| 8,182,496 B2 | 5/2012 | Rudd et al. | 606/151 |
| 2009/0099441 A1* | 4/2009 | Giszter | A61N 1/0529 607/116 |
| 2009/0326628 A1 | 12/2009 | Grandhe | 607/116 |
| 2011/0138938 A1 | 6/2011 | Giszter | 73/866.5 |
| 2012/0041531 A1 | 2/2012 | Dadd et al. | 607/137 |
| 2012/0123318 A1* | 5/2012 | Ek | A61N 1/325 604/20 |
| 2013/0190851 A1 | 7/2013 | Schouenborg et al. | 607/116 |
| 2015/0151107 A1 | 6/2015 | Schouenborg | |
| 2017/0251976 A1 | 9/2017 | Schouenborg | |
| 2017/0274201 A1 | 9/2017 | Ek et al. | |

FOREIGN PATENT DOCUMENTS

| | | |
|---|---|---|
| WO | WO 2009/075625 A1 | 6/2009 |
| WO | WO 2010/144016 A1 | 12/2010 |
| WO | WO 2012/025596 A2 | 3/2012 |
| WO | WO 2013/025678 A1 | 2/2013 |
| WO | WO 2017/048828 A1 | 3/2017 |
| WO | WO 2018/106165 A1 | 6/2018 |

OTHER PUBLICATIONS

Perumcherry Raman Sreerekha, et al., "Fabrication of Electrospun Poly (Lactide-co-Glycolide)—Fibrin Multiscale Scaffold for Myocardial Regeneration In Vitro" (2013) *Tissue Engineering: Part A*, vol. 19, Nos. 7 and 8. © Mary Ann Liebert, Inc.
Perumcherry Raman Sreerekha, et al., "A Novel Method for the Fabrication of Fibrin-Based Electrospun Nanofibrous Scaffold for Tissue-Engineering Applications" (2011) *Tissue Engineering: Part C*, vol. 17, No. 11. © Mary Ann Liebert, Inc.
C. Viney, et al., "Inspiration Versus Duplication With Biomolecular Fibrous Materials: Learning Nature's Lessons Without Copying Nature's Limitations" *Current Opinion in Solid State and Materials Science 8*; (2004) pp. 165-171.
International Search Report dated Feb. 5, 2019 in corresponding PCT International Application No. PCT/SE2018/000031.
Written Opinion dated Feb. 5, 2019 in corresponding PCT International Application No. PCT/SE2018/000031.
B.C. DiPaolo et al., "Nanofiber scaffolding for improved neural electrode biocompatibility," Proceedings of the IEEE 29th Annual Northeast Bioengineering Conference, 2003, vol. 29, pp. 21-22.

\* cited by examiner

*Primary Examiner* — H. Sarah Park
(74) *Attorney, Agent, or Firm* — OSTROLENK FABER LLP

(57) ABSTRACT

A proto-device for implantation into soft tissue comprises an oblong device body, biodegradable microfibres adhesively attached to the body, a rigid matrix of biocompatible material enclosing the body and the microfibres. The biocompatible material is dissolvable and/or degradable in aqueous body fluid at a rate substantially superior to the rate of microfibre degradation. The proto-device is one of proto-microelectrode, proto-optical fibre, proto-polymer tube for drug delivery, proto-electrical lead, proto-encapsulated electronics. Also disclosed are uses of the proto-device and methods for its implantation and manufacture.

20 Claims, 5 Drawing Sheets

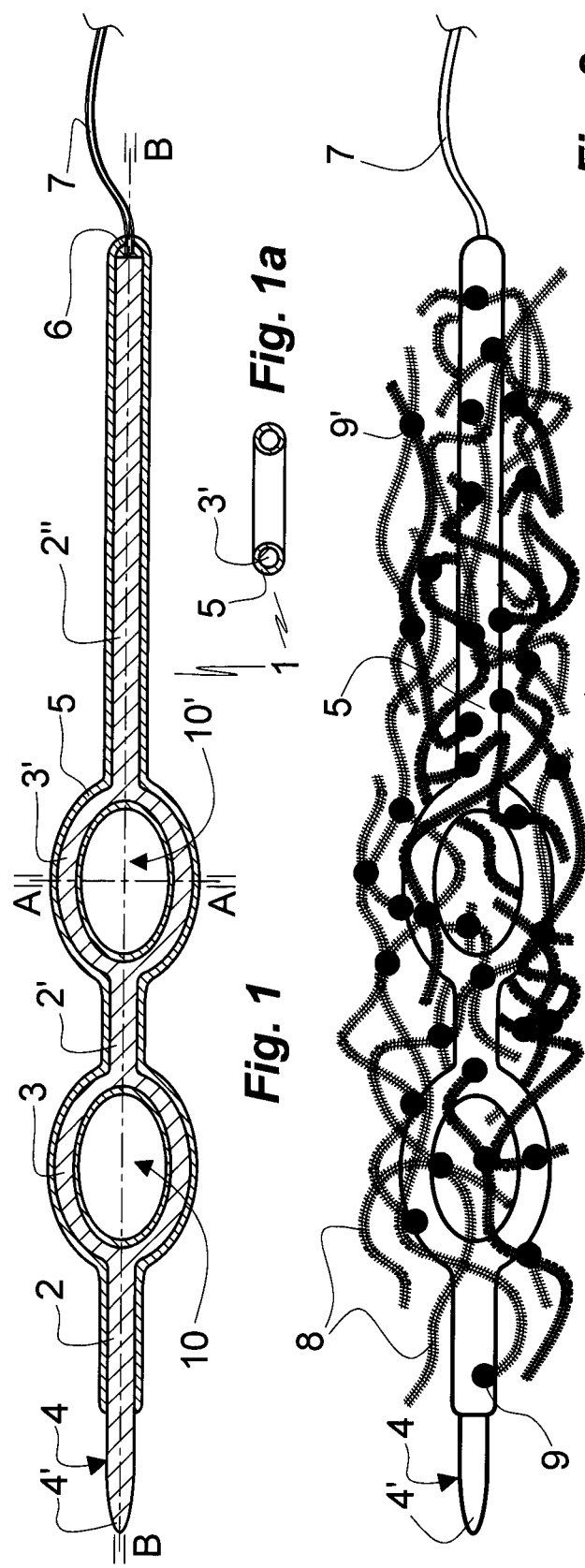
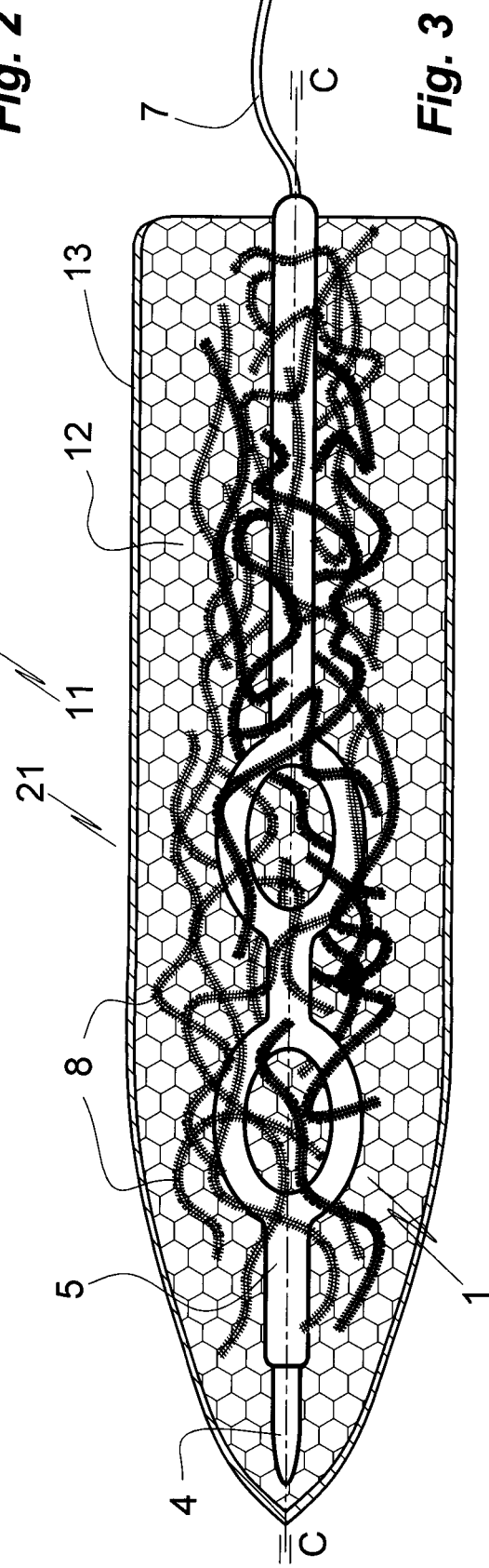

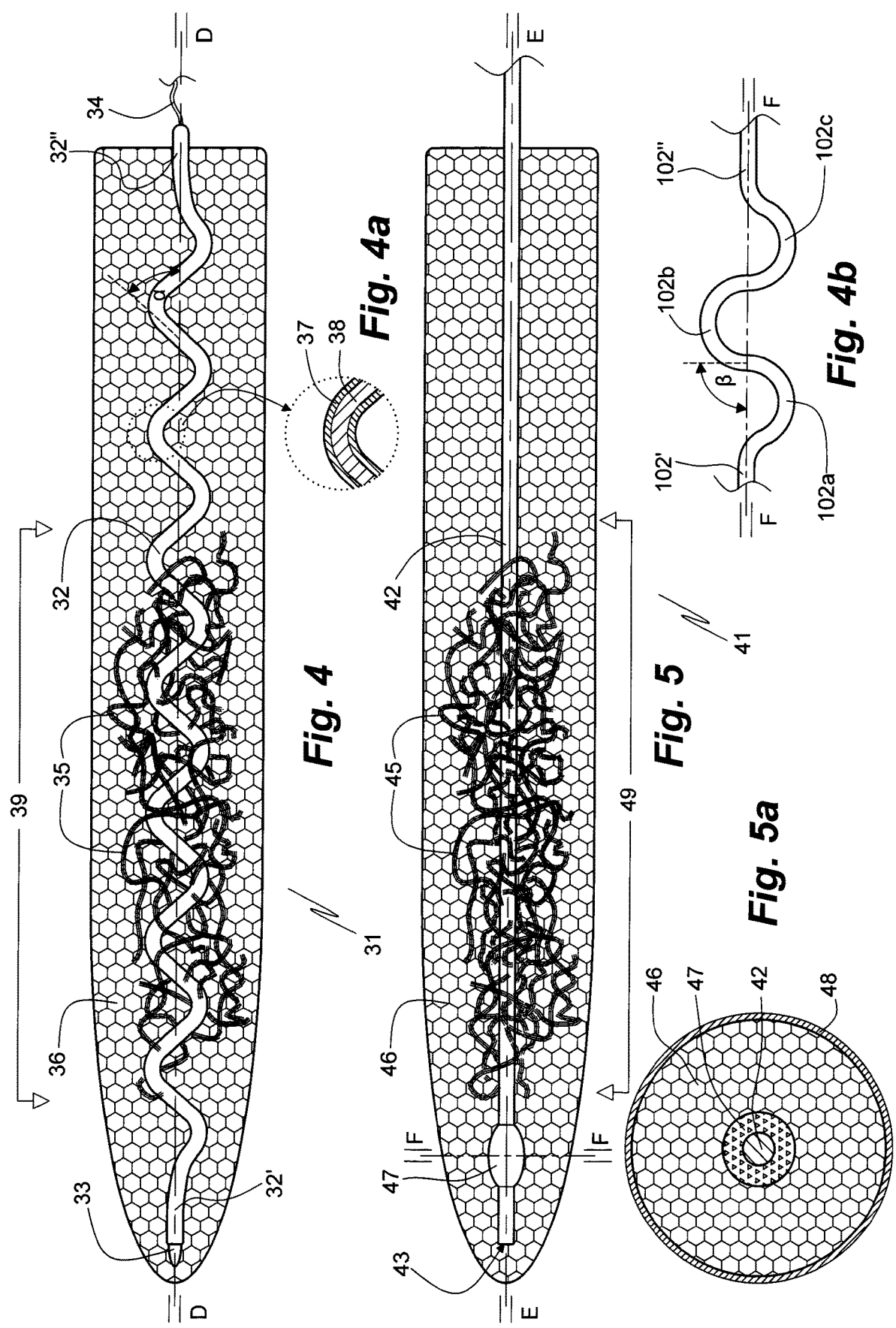

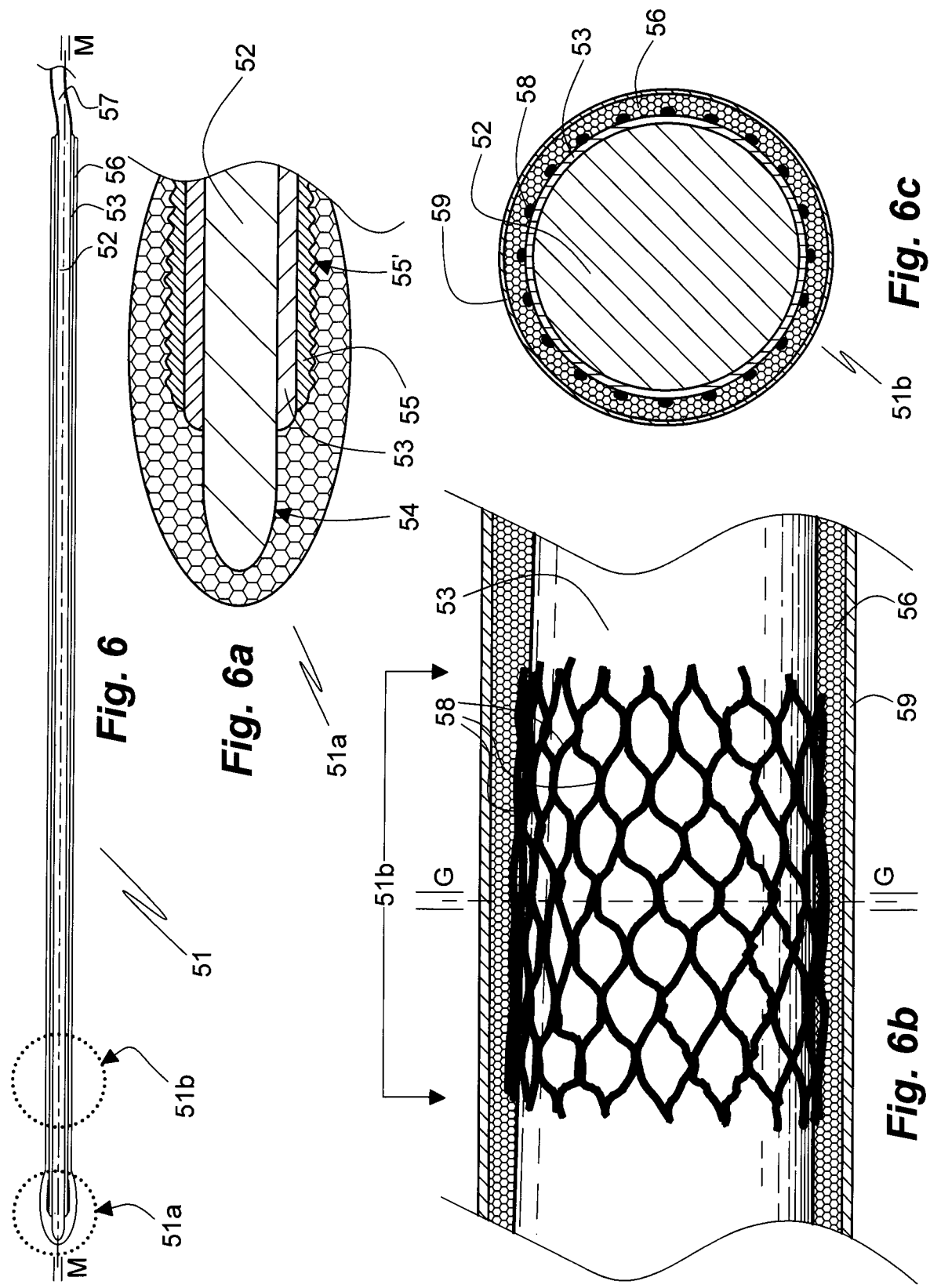

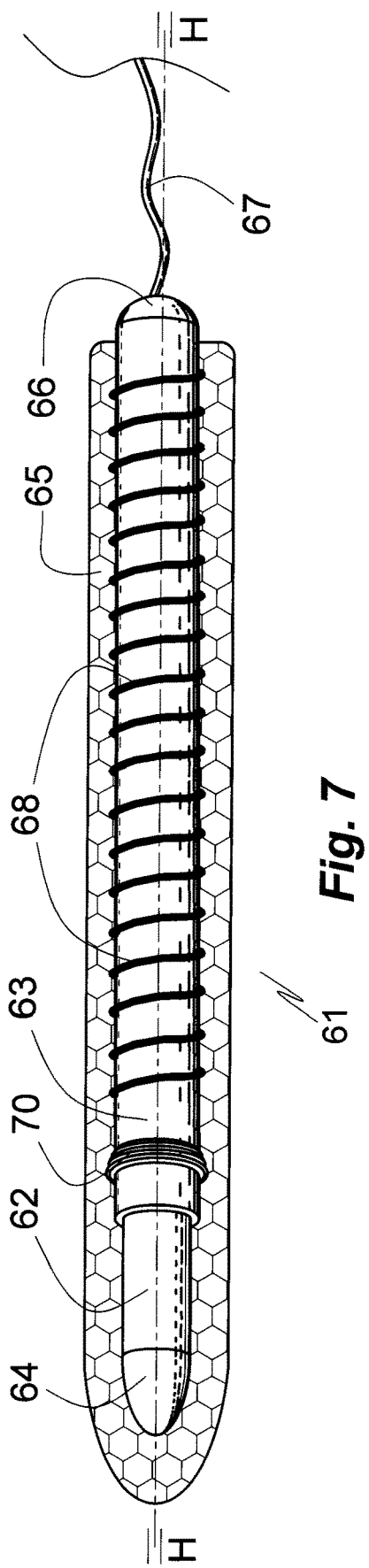
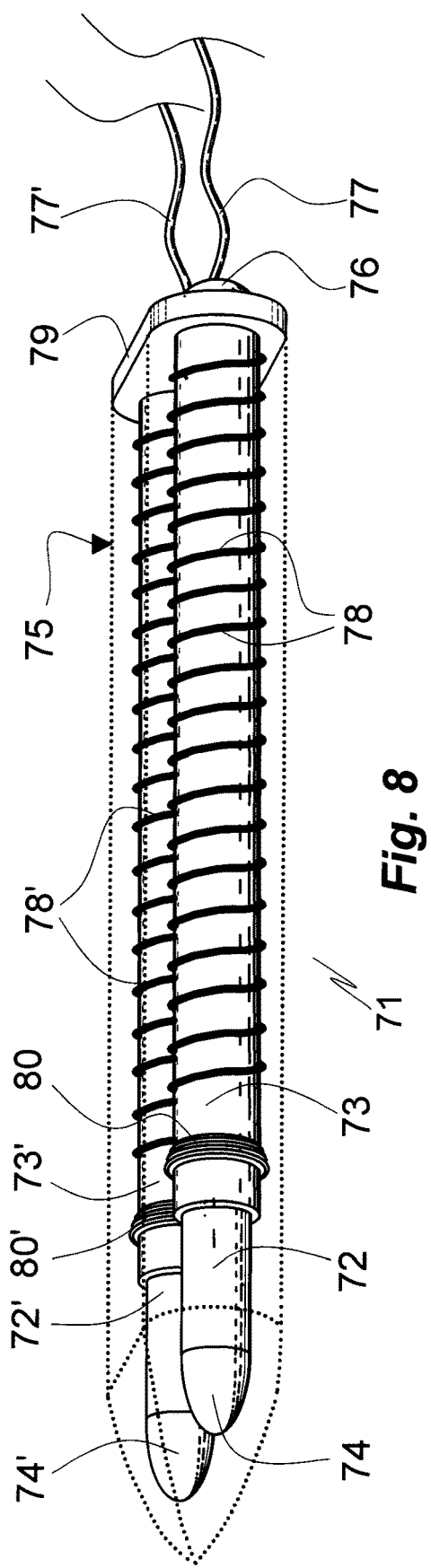
Fig. 7
Fig. 8

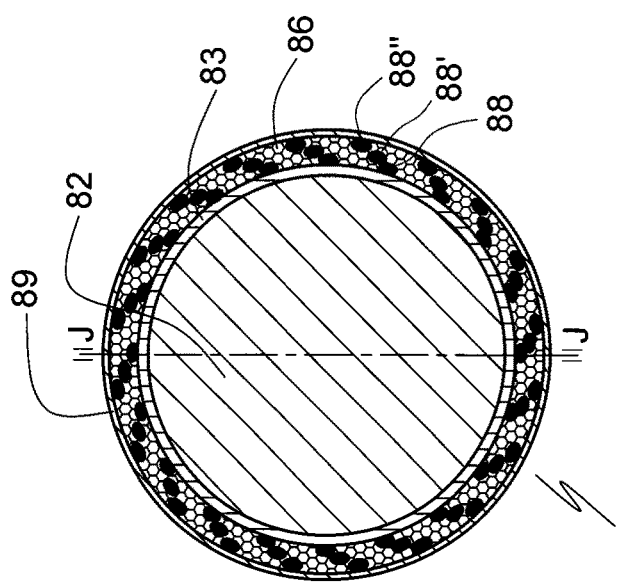
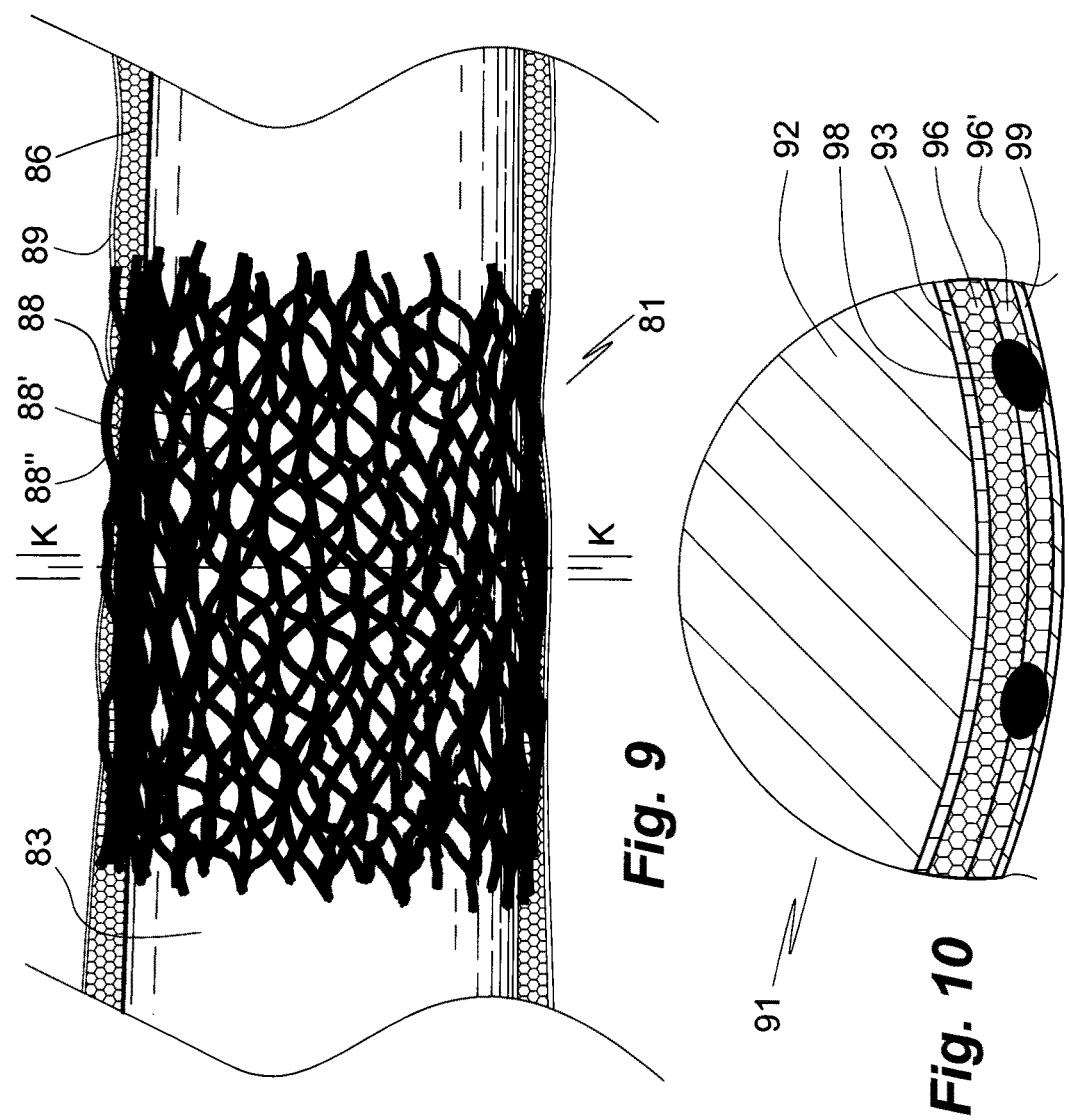

POSITIONAL STABILIZATION OF TISSUE-IMPLANTED MEDICAL DEVICES

CROSS-REFERENCE TO RELATED APPLICATIONS

The present application is a 35 U.S.C. §§ 371 national phase conversion of PCT/SE2018/000031, filed Nov. 11, 2018, which claims priority to Swedish Patent Application No. 1700274-2, filed Nov. 9, 2017, the contents of which are incorporated herein by reference. The PCT International Application was published in the English language.

FIELD OF THE INVENTION

The present invention relates to a method for positional stabilization of medical devices implanted into soft tissue by insertion into the tissue or into a channel of gel provided in the tissue. In particular, the present invention relates their positional stabilization immediately upon implantation and during a period of time following upon implantation. The present invention also relates to a corresponding means and a method for implantation.

BACKGROUND OF THE INVENTION

Implantation of medical devices or such as microelectrodes, optical microfibres, encapsulated electronics, etc. into soft tissue such as nervous or endocrine or any other kind of soft tissue damages the tissue at the implantation site. Devices of this kind are implanted as such or in form of proto-devices which are transformed to devices upon implantation. The severity of damage depends on the shape, size and surface structure of the device or proto-device and on the method of implantation. It is only upon healing of the wound caused by implantation that the medical device becomes positionally stabilized, that is, does not move in respect of the tissue but only with it. Means for long-term anchoring the device in the tissue such as protrusions or openings for ingrowth of tissue don't exert their effect immediately upon implantation of the device or transformation of an implanted proto-device into the device. During their inefficient anchoring period the device can move in the tissue and thereby even delay anchoring.

A medical device that is not positionally stabilized is prone to move differently from surrounding tissue, irritating the tissue and causing inflammation. This, in turn, delays tissue integration and jeopardizes the positional relationship between the device and particular tissue elements with which it is desired to interact actively or passively.

Tissue movements compromising positional stabilization of implanted medical devices include respiration, heart beats, bowel and muscle movements.

OBJECTS OF THE INVENTION

It is an object of the present invention to provide a method for implantation of medical devices such as microelectrodes and optical microfibres into soft tissue by which the positional stabilization of the implanted device prior to the healing of the wound caused by implantation is improved.

Another object of the invention is to provide a means for use in the method.

Further objects of the invention will become apparent from the following summary of the invention, a number of preferred embodiments thereof illustrated in a drawing, and the appended claims.

SUMMARY OF THE INVENTION

The present invention is based on the insight that, for positionally stabilizing a medical device implanted into soft tissue from the start and over a period thereafter, the provision of a temporary stabilization means is called for. The present invention is furthermore based on the insight that such a means should preferably be a temporary one to provide sufficient stabilizing effect during the period required for integration of the implanted device with the tissue, that is, for healing of the wound caused by the implantation or by surgery preceding implantation. Temporary stabilization means of this kind are also advantageous in short-term implantation when the device is not desired to be permanently anchored but is removed from the tissue a short time upon implantation, such as after an hour or a day. In parallel with progressing integration of the device into the tissue the need for anchoring decreases to finally reach a state in which a residual anchoring primarily serves for hindering the device to travel in the tissue. This kind of decrease of an anchoring capability over time facilitates removal of the device if desired, thus reducing the risk of tissue damage during removal.

More particularly, the present invention is directed to medical devices implanted into soft tissue by insertion, either by the device itself being inserted into soft tissue or by being inserted into a channel in the tissue provided by other means. A feature common to medical devices insertable into soft tissue is their oblong and distally tapering shape. Tissue-insertable devices can also take the form of proto-devices, that is, devices comprising the device to be inserted in combination with insertion promoting means. Such proto-devices, in particular in form of proto-microelectrodes, are well known in the art (WO 2009/075625 A1; WO 2010/144016 A1; WO 2012/025596 A2).

A useful means for positionally stabilizing a proto-device for implantation of soft tissue according to the invention are biocompatible microfibres attached to the surface of the device and capable of being degraded upon implantation by contact with aqueous body fluid, in particular capable of being degraded and resorbed over a period at least corresponding to the period of time required for positional stabilization of the device by integration into the tissue. Microfibres for use in the invention are preferably degradable by hydrolysis, in particular by enzymatically enhanced hydrolysis. It is particularly preferred for microfibres of the invention to be used in form of non-woven microfibre aggregates. Non-woven microfibre aggregates consist of irregularly intertwined microfibres and may comprise microfibres attached to each other in an irregular manner such as by attachment caused by local melting and/or by gluing with a biocompatible glue.

The time for positional stabilization by integration may range from a few days, such as 2 or 5 or ten days to a couple of weeks, such as 2 or 5 weeks, and occasionally even a few months. Degradable microfibres of this kind are known in the art, such as microfibres of polylactide and poly(lactide-co-glycolide), polyvinyl acetate and polyvinyl alcohol and their cross-linked modifications, the molecular weight of which can be varied to provide for suitable rates of degradation. Other microfibres for use in the invention are natural and synthetic proteinaceous microfibres, such as fibrin microfibres, collagen microfibres, laminin microfibres, fibronectin microfibres, cross-linked gelatin microfibres, silk microfibres produced from aqueous protein solutions as disclosed by Viney C and Bell F I (Curr Opin Solid State Mater Sci. 8 (2005) 164-169) but also inorganic microfibres such phosphate glass microfibres, for instance $P_{40}Na_{20}Ca_{16}Mg_{24}$ phosphate glass microfibres disclosed in U.S. Pat. No. 8,182,496 B2.

By their attachment to the surface of the device the biocompatible microfibres increase that surface and make it irregular. The thus increased and irregular surface of the device adheres more easily to the surface of the tissue to which it abuts. Microfibres of the invention are in the micro- or nanometer diameter range.

Particularly preferred are electrospun microfibres and electrospinning is a preferred method for producing microfibres of the invention. It is within the ambit of the invention to provide the device with a net of fibrin microfibres by electrospinning fibrinogen, such as by the method of S R Perumcherry et al. disclosed in Tissue Eng Part C Methods 17; (2011) 1121-30 or with a net of poly(lactide-co-glycolide)/fibrin microfibres such as one disclosed by Perumcherry et al. in Tissue Eng Part A 19; 7-8(2012) 849-859. A self-assembling fibrin net can also be produced by applying an aqueous solution of fibrinogen and thrombin rich in calcium directly to a microelectrode, then cross-linking the microfibres by applying an aqueous solution of plasma transglutaminase and/or factor XIII on the newly formed net for crosslinking.

It is preferred for a microfibre to be selected from proteinaceous microfibre and polyester fibre. Preferred fibrous materials include those based on poly(lactide), poly(lactide-co-glycolide), poly(glycolide), electrospun albumin, mucus material rich in glycoprotein. A particularly preferred kind of microfibres are electro-spun microfibres. According to preferred aspect of the invention the microfibres form a non-woven irregular structure. It is preferred for a microfibre to be adhesively attached to a microelectrode and to one or more other microfibres. Preferably the microfibres are disposed along 50% or more of the axial extension of a microelectrode. Microfibres for use in the invention can be of a resilient or a non-resilient material.

According to the present invention thus is provided a proto-device for implantation into soft tissue, in particular nervous or endocrine tissue, selected from the group consisting of proto-microelectrode, proto-optical fibre, proto-polymer tube for drug delivery, proto-electrical lead, proto-encapsulated electronics, comprising an oblong device body having a proximal end, a distal end, and a central axis, comprising biodegradable microfibres adhesively attached to the device body, wherein a microfibre is biodegradable in the tissue within a period of one or two weeks or one month or two months from implantation;

comprising a rigid matrix of biocompatible material having an outer face and enclosing the device body and the microfibres; wherein the rigid matrix of biocompatible material is dissolvable and/or degradable in aqueous body fluid at a rate superior to the rate of microfibre degradation by a factor of 2 or 5 or 10 or 20 or, in particular, of 100 or more;

comprising a means for supporting permanent positional stabilization upon biodegradation of the microfibres comprised by the device body or attached to an outer face thereof, wherein the means is selected from the group consisting of: rugged surface of the device body, knobby retainer optionally comprising a rugged surface attached to device body, eye, loop or bent section of the device body, wherein the bending section is bent away from the central axis by an angle of 15° or more, in particular by an angle of 30° or more.

It is preferred that at least 80%, in particular at least 90% or 95% or 99% or 100% of the microfibres are biodegradable in the tissue within a period of one or two weeks or one month or two months from implantation.

Preferred microfibres for use in the invention comprise synthetic polymer fibres such as polylactide fibres, poly (lactide-co-glycolide) fibres, polyglycolide fibres, polyvinyl acetate fibres, polyvinyl alcohol fibres; natural and synthetic proteinaceous fibres, such as albumin fibres, fibrin fibres, collagen fibres, laminin fibres, fibronectin fibres, cross-linked gelatin fibres, silk fibres, glycoprotein fibres; inorganic fibres such as phosphate glass fibres. A biodegradable microfibre can also be a crosslinked, that is, of a crosslinked material.

According to a first preferred aspect of the invention the microfibres or a portion thereof are dispersed in the rigid matrix, such as at least 50% or 80% or 90% or even more than 95% of the microfibres.

According to a second preferred aspect of the invention the microfibres are additionally attached adhesively to each other.

The rigid matrix consists of or comprises preferably one or more members of the group consisting of: low molecular carbohydrate, in particular monosaccharide or disaccharide, proteinaceous material, in particular gelatin.

According to a third preferred aspect of the invention a majority of the microfibers, such as more than 50% or more than 80% of the microfibers, is disposed near the outer face of the rigid matrix that is, at an average distance from the outer face of the device corresponding to their two-fold or five-fold average distance from an outer face of the device.

It is preferred for the rigid matrix to be disposed rotationally symmetrically or about rotationally symmetrically in respect of a longitudinal axis of the device body.

According to a third preferred aspect of the invention a glidant layer facilitating insertion into tissue is disposed on the outer face of the rigid matrix. The glidant layer can additionally be capable of delaying access of aqueous body fluid to the rigid matrix during implantation so as to prevent premature its premature dissolution.

According to a fourth preferred aspect of the invention the proto-device comprises a means for supporting permanent positional stabilization attached to an outer face of the device body, in particular a means for increasing the surface of the device body, such as a rugged or knobby stabilization element. The means for supporting permanent positional stabilization is preferably arranged at a distal portion of the device body, in particular fully or partially surrounds a distal portion thereof.

Alternatively or additionally, the means for supporting permanent positional stabilization can have the form of an eye or loop formed by the device body and be preferably disposed at a distal portion thereof. They may also have the form of a bent section of the device body with a bending angle of 15° or more. The retainer means can also comprise or consist of a coat of cell adhesion promoting material on the device body such as L1 protein or neural cell adhesion molecule.

Due to the ingrowth of adjacent tissue, that is, by adjacent tissue closing in on the implanted device, the force needed for positional stabilization of an implanted device of the invention diminishes over time. This allows the device retaining effect of the means for positional stabilization to decrease over time, that is, to be temporal rather than permanent. While a useful rate of decrease of the device retaining effect, that is, the positional stabilizing effect, can vary depending on the kind and properties of the implanted device, a general measure of such decrease will be a reduction by 50% or more one or two months from implantation, and may even reach 80% or 90%.

According to the present invention is furthermore provided a proto-device for implantation into soft tissue such as nervous tissue in form of a proto-microelectrode comprising an oblong electrically conducting core having a proximal end and a distal end, one or more insulating layers on a portion of the core extending from the proximal end thereof towards the distal end, wherein the fibres are adhesively attached to the insulating layer and/or the core and, optionally, to each other. It is preferred for a diameter of the core or the combination of core and insulating layer(s) to be 100 µm or less, in particular 35 µm or less, more preferred 15 µm or less or even 8 µm or less. The diameter of the core or the combination of core and insulating layer(s) can vary in a distal-proximal direction, in particular increase in a distal direction. The core is preferably of metal or comprises metal, in particular a noble metal such as gold, platinum or iridium and their alloys. Alternatively or additionally, the core consists of or comprises electrically conducting polymer and/or electrically conducting carbon such as graphite or graphene. An insulating layer preferably comprises or consists of polymer material, in particular one selected from the group consisting of Parylene, polyurethane, silicone. According to a further preferred aspect of the invention the core is extendable in an axial direction and/or is flexible. The core is preferably in wire or ribbon form. However, any other oblong cores can be used in the invention, such as axially extensible cores of, for instance, meander form, and hollow cores. A suitable electrically conducting polymer core material is poly(3,4-ethylenedioxythiophene (PEDOT). Furthermore, the microelectrode body may comprise electrically conducting carbon such as graphite or graphene, optionally in form of nanotubes. A preferred electrode body insulating material is Parylene. Other preferred electrode body coating materials are polyurethane and silicone but other biocompatible polymer materials may be used as well. Appropriate inorganic materials for electrical insulation such as hafnium oxide can also be used. A preferred method of electrode body coating with insulating material is by vapour phase deposition.

A microelectrode of the invention can be essentially straight but may alternatively comprise bent portions allowing its extension in an axial (proximal-distal) direction. Preferred are bent portions with a bending angle of 15° or more. Axially extendable electrodes for use in the invention, such as electrodes comprising meander-formed sections, are disclosed in WO 2009/075625, which is incorporated herein by reference.

Encapsulated electronics of the invention can, for instance, comprise electronics for electrical stimulation of cells or for recording electrical signals emitted from nerve cells. The use of two or more medical devices for simultaneous implantation and positional stabilization is also comprised by the invention, such as implantation and positional stabilization of bundles and arrays of microelectrodes and/or optical and/or other devices of the invention.

According to the present invention is also provided a method for implantation of a proto-device of the invention, in particular of a proto-microelectrode of the invention, comprising inserting, with its distal end foremost, the device into soft tissue or into a pre-formed channel in the tissue filled with an aqueous gel, controlling the position of the inserted device during a period of time extending from insertion until disposition of the microfibres between the insulating layer and the tissue in a manner so as to make the microfibres form a layer abutting the insulating layer and the tissue.

According to a preferred aspect of the method for implantation, the rate of insertion decreases with implantation depth. It is preferred for the average rate of insertion during insertion from 0% to 50% of the final depth to be at least twice as high, preferably trice as high, as the average rate of insertion from 50% to 100% of the final depth. It is also preferred for the insertion rate during insertion from 0% to 80% to be higher by a factor of 5 or 10 than the insertion rate during insertion from 80% to 100%, in particular during insertion from 90% to 100%.

The proto-device of the present invention, in particular a proto-microelectrode, can be used in the treatment of an endocrine disorder or nervous disorder, such as in an endocrine disorder selected from the group consisting of acromegaly, Addison's disease, adrenal disorder, Cushing's syndrome, diabetes, growth disorder, hyperglycemia, hypoparathyroidism, hypothyroidism, metabolic syndrome, osteoporosis, pituary disorder, thyroid disease, or in the treatment of a nervous disorder selected from the group consisting of Alzheimer's disease, amnesia, aphasia, apraxia, Asperger syndrome, ataxia, bipolar disorder, brain damage, carpal tunnel syndrome, central pain syndrome, chronic fatigue syndrome, chronic pain, coma, Creutzfeldt-Jakob disease, Cushing's syndrome, disorders of consciousness, diabetic neuropathy, Down syndrome, epilepsy, fibromyalgia, functional neurological disorder, Guillain-Barré syndrome, headache, hereditary motor neuropathy, inflammatory myopathy, lumbar disc disease, lyme disease, meningitis, migraine, motor neurone disease, muscular dystrophy, myalgic encephalomyelitis, myopathy, narcolepsy, neuropathy, neurosis, Parkinson's disease, paroxysmal attacks, phantom limb, postherpetic neuralgia, reflex neurovascular dystrophy, sleep apnea, spinal cord injury, stroke, tremor, whiplash.

According to the present invention is additionally provided a method of manufacture of the proto-device of the invention, comprising providing the device; adhesively attaching biocompatible microfibres to a portion of the device and to each other; immerging the combination of device and microfibres into an aqueous solution of a biodegradable proteinaceous or carbohydrate material; drying the combination; optionally covering an outer face of the combination with a material preventing premature dissolution of the rigid matrix during insertion into soft tissue, such as a wax or a triglyceride melting slightly above body temperature. An advantageous modification of the method is to cool the proto-microelectrode prior to insertion to a temperature near 0° C., such as a temperature between 0° C. and 5° C., or to an even lower temperature below 0° C. It is preferred for the device to be one of: microelectrode, optical fibre, polymer tube for drug delivery, electrical lead, encapsulated electronics; particularly preferred is a device in form of a microelectrode.

The invention will now be explained in more detail by reference to a number of preferred embodiments illustrated in a drawing, which is not to scale and only intended to illustrate design principles of the devices of the invention.

DESCRIPTION OF THE FIGURES

FIG. 1 represents a first embodiment of the microelectrode of the invention for use in the invention in an axial section B-B comprising two eyes for tissue ingrowth;

FIG. 1a is a radial section A-A of the microelectrode of FIG. 1;

FIG. 2 represents a combination of the microelectrode of FIG. 1 and microfibres surrounding and attached to it, in a side view perpendicular to the eyes;

FIG. 3. represents a first embodiment of the proto-microelectrode of the invention formed by incorporating the combination of microelectrode and microfibres embedded in a rigid matrix of a material dissolvable in aqueous body fluid, in the same view as in FIG. 2, with the rigid matrix in a transparent presentation. The rigid matrix is shown translucent.

FIG. 4 represents a second embodiment of the proto-microelectrode of the invention comprising an axially extendable electrode body, in the same view as FIG. 3.

FIG. 4a is a partial enlarged view of FIG. 4, in the same section.

FIG. 4b represents a variety of the embodiment of FIGS. 4, 4a, in a partial enlarged view and in the same section.

FIGS. 5, 5a represent an embodiment of a proto-optical fibre of the invention to which microfibres degradable in aqueous body fluid are attached and which is embedded, in combination with said microfibres, in a rigid matrix of a material dissolvable in aqueous body fluid. FIG. 5 is an axial section E-E corresponding to that of FIG. 4 while FIG. 5a is a radial section F-F.

FIGS. 6-6c illustrate a third embodiment of the proto-microelectrode of the invention formed by providing a microelectrode (FIGS. 6, 6a) with a net of biodegradable microfibres enclosing a section of its elongated body (FIGS. 6b, 6c, axial section M-M, FIG. 6). FIG. 6b is a side view partial in section of the electrode section covered with the net of biodegradable microfibres of which a radial section (G-G, FIG. 6b) is shown in FIG. 6c in a state embedded in a rigid matrix of a material degradable or dissolvable in aqueous body fluid and with the rigid matrix provided with an outer layer of a material delaying contact of the rigid matrix with aqueous body fluid.

FIG. 7 represents a fourth embodiment of the proto-microelectrode of the invention, in the same view as the partial view of FIG. 6b and with the net of microfibres thereof substituted by a single microfibre spiral wound around the electrode body. The matrix dissolvable in body fluid surrounding the microelectrode is shown translucent.

FIG. 8 represents a proto-microelectrode bundle of the invention comprising two microelectrodes of the kind shown in FIG. 7 and in the same view, surrounded by a common matrix dissolvable in aqueous body fluid;

FIGS. 9 and 9a represent a variety of net of biodegradable microfibres covering a portion of the insulated body of a proto-microelectrode shown in FIGS. 6b, 6c or covering a portion of a proto-optical fibre, the net being layered and extending to from the insulation layer to the outer face of the biodegradable and/or biodegradable matrix layer, in the same section, respectively;

FIG. 10 represents an enlarged section of a variety of the proto-microelectrode of the of FIGS. 6b, 6c comprising two biodegradable matrix layers, a portion of the fibrous net also being disposed in the outer layer, in the same view as in FIG. 6b.

DESCRIPTION OF PREFERRED EMBODIMENTS

Example 1

FIGS. 1, 1a illustrate a first embodiment 1 of a microelectrode of the invention comprising two eyes 10, 10', a distal eye 10 and a proximal eye 10' separated by a straight intermediate section 2'. From the distal end of the distal eye 10 extends a straight distal section 4 ending in a distal tip 4'. From the proximal end of the proximal eye 10' extends a straight proximal section 2" at the proximal end of which a flexible lead 7 is attached by solder 6. The microelectrode 1 is cylindrical in a radial section. It comprises an electrically conducting core 2, 2', 2", 3, 3' of metal or electrically conducting polymer covered, except for the tip 4' and a portion of the distal section 4 extending from the tip 4' in a proximal direction, by an insulation layer 5 of a non-conducting material, in particular a non-conducting polymer. The co-planar distal and proximal eyes 10, 10' are designed for long-term positional stabilization by tissue ingrowth. The eyes 10, 10' can be made by laser milling prior to applying the insulation layer 5. The flexible lead 7 provides electrical connection with an electrode control unit (not shown). Alternatively, the flexible lead 7 can be integral with the core 2, 2', 2", 3, 3'. The microelectrode is rotationally symmetric in respect of its central longitudinal axis B. FIG. 1a is a radial section A-A (FIG. 1) of the second eye 3'.

FIG. 2 illustrates a combination 11 the microelectrode 1 of the invention and an irregular fibrous enclosure formed by single microfibres 8 of cross-linked gelatin adhesively attached by electrospinning to the outer face of the electrode insulation layer 5 at points of attachment 9 and to each other at points of attachment 9'. The distal, non-insulated section 4 of the core 2, 2', 2", 3, 3', 4 (FIG. 1) comprising the distal tip 4' has no microfibres 8 attached to it.

The first embodiment of a proto-microelectrode 21 of the invention shown in FIG. 3 has been obtained by enclosing by a mould, preferably a of a gas permeable material, to a depth close to its proximal end the combination of microelectrode 1 and microfibre 8, filling the interstice between the combination 1, 8 with a concentrated aqueous solution of glucose comprising a gelling agent such as gelatin of Bloom strength 80-300, evaporating water at reduced pressure and/or a temperature above ambient to form a rigid matrix layer 12 on the microelectrode 1 in which the microfibres 8 are disposed. Then a dissolution retarding and gliding enhancement layer 13 of a triglyceride is applied by spray coating or dip coating to the distal and lateral faces of the rigid matrix layer 12 thus formed.

The proto-microelectrode 21 is rotationally symmetric in respect of its longitudinal axis C-C, which is coincident with the longitudinal axis B-B of the microelectrode 1. FIG. 3 is a sectional axial view in regard of the matrix layer 12 and the retarding and gliding enhancement layer 13 and a side view in regard of the combination 11 of FIG. 2 incorporated in the matrix layer 12. Points 9 of microfibre attachment and the soldering point 6 have been omitted in FIG. 3.

Example 2

FIG. 4 illustrates, in a side view, a second embodiment 31 of the proto-microelectrode of the invention comprising a microelectrode 33, 32', 32, 32" of which sections 32', 32, 32" are insulated while its distal terminal section 33 is free of insulation. The central flexible zigzag-formed section 32 and short straight distal and proximal terminal sections 32', 32" are centred in respect of electrode axis D-D. The zigzag-formed sections 32 include an angle α of about 45° with the axis D-D.

FIG. 4a is a partial enlarged view of the microelectrode 33, 32', 32, 32" in the same axial section as in FIG. 4, illustrating a bend 38 of the central section 32 with the insulation layer 37 on the electrode body 38 shown. The insulation layer 37 covers the entire body 38 of the microelectrode 33, 32', 32, 32" except for the distal tip 33. The electrode body 38 is about cylindrical in a radial section but may alternatively have any other form in a radial section, which is however not preferred. A flexible lead 34 attached to the electrode body 38 at the proximal end of the proximal section 32" by soldering or welding provides electrical connection with an electrode control unit (not shown). A distal portion of the central section 32 is surrounded by microfibres 35 of cross-linked gelatin, which are adhesively attached to the insulation 37 and to each other so as to form a layer or fleece or net of non-woven 35, also shown in a side view in FIG. 4. The second embodiment 31 of the proto-microelectrode of the invention is obtained in a manner similar to that used to produce embodiment 21 of Example 1. The matrix layer 36 of glucose comprising a gelling agent such as gelatin is disposed about rotationally symmetric around a distal portion 39 of wave-formed electrode section 32. The matrix layer 36 is about rotationally symmetric in respect of the electrode axis D-D and narrows in a distal direction so as to provide the proto-microelectrode 31 with a blunt distal tip. Not shown in FIG. 4 is a solder/welding point disposed at the proximal end of the electrode body 38 by which the flexible lead 34 for connecting the electrode body 38 to a control unit is attached to the electrode body 38.

FIG. 4b is a partial view of a modification of the microelectrode 33, 32', 32, 32" of FIG. 4, from which it differs only by the geometry of bends 102a, 102b, 102c, which extend between straight distal and proximal sections 102', 102" centred in respect of an axis F-F. The bends 102a, 102b, 102c include an angle β of 90° with the axis F-F.

Example 3

FIGS. 5, 5a illustrate a proto-optical fibre 41 of the invention comprising a central optical fibre 42 of glass or a translucent polymer material ending in a flat tip 43 from which radiation conducted by the optical fibre 42 exits in a distal direction. The optical fibre 42 is rotationally symmetric in respect of its central longitudinal axis E-E. A central portion 49 of the optical fibre 42 is surrounded by filaments 45 of cross-linked gelatin adhesively attached to the optical fibre 42 and to each other so as to form a layer or fleece of non-woven 45. The proto-optical fibre 41 of the invention is obtained in the same manner as the first embodiment 21 of the proto-microelectrode of the invention illustrated in Example 1. The matrix layer 46 of glucose comprising a gelling agent such as gelatin is disposed rotationally symmetric around the optical fibre 42 axis E-E and narrows in a distal direct so as to provide the proto-optical fibre 41 with a blunt distal tip. At a distal section intermediate between the distal end 43 of the optical fibre 42 and the portion 49 of the optical fibre 42 surrounded by microfibres 45 the optical fibre 42 extends through and adheres to a retainer 47 of a polymer material that is not degradable in aqueous body fluid or the rate of degradation of which is substantially smaller than that of the microfibres 45. The aim with the retainer 47 is to provide additional positional stabilization upon insertion of the proto-optical fibre 41 into soft tissue and dissolution/degradation of its matrix layer 46 and fibrous net 45; for improved tissue adhesion it can be coated with L1 protein or neural cell adhesion molecule 1 or other another cell adhesion promoting material. The view of FIG. 5 corresponds to that of FIG. 4.

FIG. 5a is a radial section F-F through at the proto-optical fibre 41 at the retainer 47 level, also illustrating a dissolution retarding/friction decreasing triglyceride layer 48 on the matrix 46 omitted in FIG. 5.

Example 4

The elongated proto microelectrode 51 of FIGS. 6, 6a comprises an electrically conducting electrode body 52 covered, except for a distal terminal portion 54 thereof, with a layer 53 of insulating polymer material. The electrode body 52 and the flexible lead 57 providing electrical contact with an electrode control unit (not shown) are distal and proximal portions of a single metallic wire 52, 57, the flexible lead portion 57 also being covered with the layer 53 of insulating polymer material. Near its distal end the insulating layer 53 is provided with a polymer sleeve 55 extending around its periphery. The sleeve 55 has a rugged surface 55' which assists in positionally stabilizing the electrode 51 in the tissue upon dissolution in aqueous body fluid of a matrix 56 of glucose and gelatin covering the insulated and non-insulated portions of the electrode body 52 and the sleeve 55. FIG. 6a is an enlarged view of the distal terminal portion 51a of the proto microelectrode 51.

FIG. 6b shows, in a side view, an insulated section 51b of the electrode body 52 disposed proximally of the sleeve 55. The insulated section 51b is provided with a net 58 of biodegradable polymer microfibres attached to its surface and extending circumferentially so as to enclose the insulated section 51b. While the insulated section 51b provided with the fibrous net 58 is shown in a side view the matrix layer 58 disposed thereon is shown in an axial section (axis F-F, FIG. 6) as is the optional layer 59 of a material delaying contact of the rigid matrix 56 layer with aqueous body fluid, for instance a layer of a lipid melting at a temperature slightly above body temperature.

FIG. 6c shows a radial section (G-G) of the portion 51b of the insulated 53 electrode body 52 provided with the net 58 of biodegradable microfibres enclosed by the matrix layer 56. In the event that the rigid matrix layer 56 consists of or comprises a biodegradable material it is mandatory that the biodegradation rate of the material(s) forming the matrix layer 56 is substantially higher than that of the material from which the microfibres 58 are formed.

Example 5

FIG. 7 shows a rotationally symmetric (longitudinal axis H-H) elongate microelectrode 62, 63, 64, 66, 68, 70 incorporated into a stiff, water soluble or degradable matrix 65 so as to form a proto microelectrode 61 of the invention.

Instead of the net 58 of biodegradable microfibres of the proto-microelectrode of FIGS. 6b, 6c the proto-microelectrode 62, 63, 64, 66, 68, 70 is provided with a single biodegradable microfibre 68 or a thread 68 of a multitude of biodegradable microfibres disposed on the insulation layer 63 of the microelectrode body 62 in form of a coil 68. The coil 68 is fastened on the insulation layer 63 at least at both ends (not shown) but may also be fastened at points intermediate between the ends. The electrode body 62 of the rotationally symmetric proto-microelectrode 61 comprises non-insulated distal body portion ending in a tip 64. At its insulated proximal end 66 a flexible insulated electrical lead 67 is attached to the electrode body to provide for electrical connection with a control unit (not shown). A sleeve 70 of polymer material is attached to a frontal portion of the insulation layer 63 from which it extends in a radial direction. The sleeve 70 has a rugged surface to provide for enhanced contact with abutting soft tissue to improve positional stability of the microelectrode 62, 63, 64, 66, 68, 70 prior to and upon degradation of the coiled biodegradable microfibre 68 preceded by dissolution of the matrix 65 in which the microelectrode 62, 63, 64, 66, 68, 70 with the coiled microfibre or thread 68 is embedded.

Example 6

FIG. 8 shows a proto microelectrode bundle 71 comprising a first microelectrode 70, 72, 73, 74, 76, 77, 78, 80 and a second microelectrode 70', 72', 73', 74', 76', 77', 78', 80' of identical shape of the same kind as the microelectrode of FIG. 7 mounted at their proximal ends in a through bores of a stiff polymer base 79 from which they extend in parallel. Features 70, 72, 73, 74, 76, 77, 78, 80 and 70', 72', 73', 74', 76', 77', 78', 80' correspond to features 62, 63, 64, 66, 67, 68 and 80 of the microelectrode of FIG. 7. The proto-microelectrode bundle 70, 72, 73, 74, 76, 77, 78, 80; 72', 73', 74', 76', 77', 78', 80' is enclosed by in a matrix 75 of a biocompatible water soluble agent, for instance glucose or glucose comprising gelatin. The matrix 75 can be covered by a thin layer of a dissolution delaying material (not shown in FIG. 8), such as a triglyceride of a melting point above body temperature.

Example 7

FIG. 9 shows a side view and FIG. 9a a radial section K-K of an insulated portion of a proto-microelectrode 81 of the invention of oblong cylindrical form covered by three layers of a net of microfibres 88, 88', 88" which are biodegradable in aqueous body fluid, an inner layer 88, an intermediate layer 88' and an outer layer 88". The layers 88, 88', 88" may be interconnected or not. The innermost layer 88 covers and adheres to the polymer insulation layer 86 covering the electrically conducting electrode body 82. The layers 88, 88', 88" are embedded in a matrix 86 of a biocompatible material which is dissolvable or degradable in aqueous body fluid, such as a matrix of low molecular weight carbohydrate or protein, for instance glucose or gelatin. The matrix 86 resides on a layer 83, and is covered by a thin coat 89 of, for instance, a lipid melting above body temperature covering the outer face of the matrix 86 layer to protect it from premature dissolution or degradation by aqueous body fluid. A multi-layered coat of this kind can also be applied to an optical fibre, directly on the fibre, on a light reflecting coat covering the optical fibre or on any other implantable proto device of the invention.

Example 8

A variety 91 of the proto-microelectrode of FIGS. 6-6c is illustrated in FIG. 10 in a partial sectional view, enlarged; the view of FIG. 10 corresponds about to that of FIG. 6c. The proto-microelectrode 91 differs from that of FIGS. 6-6c by the matrix comprising to sections, an inner section 96 and an outer section 96', which can be of same or different material. Upon application of the inner section 96 on the insulation layer 93 covering the electrically conducting electrode body 92 the inner section 96 is covered with a net of microfibres 98, which may advantageously be applied when the inner section 96 is not fully dried, that is, is somewhat sticky. Instead of the net of microfibres several layers of the fibrous net 98 or a fibrous fleece may be applied on the inner section 96, which then is covered by a thin outer section 96' of same or different material, in particular of a material of a higher dissolution rate in aqueous body fluid than the material of the inner section 96. The outer section 96' can be covered by a layer 99 of a material delaying access of aqueous body fluid to the outer layer 96' to prevent its premature dissolution during implantation.

The invention claimed is:

1. A proto-device for implantation into soft tissue, the proto-device comprising:
    an oblong device body, comprising a microelectrode comprising an electrically conductive core having a proximal end and a distal end, and at least one insulating layer on a portion of the core extending from the proximal end towards the distal end;
    biodegradable irregularly intertwined microfibers adhesively and irregularly attached to the insulating layer and/or the core of the microelectrode, wherein each of the microfibers is biodegradable in the soft tissue within a period selected from the group consisting of one week, two weeks, one month and two months from the implantation of the proto-device; and
    a rigid matrix of biocompatible material having an outer face and the rigid matrix enclosing the microelectrode and the microfibers with a portion of the microfibers dispersed in said rigid matrix; wherein the rigid matrix of biocompatible material is dissolvable and/or degradable in aqueous body fluid at a rate greater than the rate of microfiber degradation by a factor of at least 2 and up to a factor of about 100;
    wherein the microelectrode has at least one means for supporting permanent positional stabilization of the microelectrode in the soft tissue upon biodegradation of the microfibers selected from the group consisting of a rugged surface of the device body, a knobby retainer comprising a rugged surface attached to the microelectrode, an eyelet, a loop or a bent section of the microelectrode, wherein the bent section is bent away from the central axis of the microelectrode by an angle of at least 15°.

2. The proto-device according to claim 1, wherein at least 80%, of the microfibers are biodegradable in the soft tissue within a period of up to about month from implantation.

3. The proto-device according to claim 2, wherein the biodegradable microfibers are selected from the group consisting of a synthetic polymer fiber selected from the group consisting of polylactide fiber, poly(lactide-co-glycolide) fiber, polyglycolide fiber, polyvinyl acetate fiber, polyvinyl alcohol fiber; a natural and synthetic proteinaceous fiber, selected from the group consisting of albumin fiber, fibrin fiber, collagen fiber, laminin fiber, fibronectin fiber, cross-linked gelatin fiber, silk fiber, glycoprotein fiber; an inorganic fiber and phosphate glass fiber; a biodegradable microfiber and a crosslinked microfiber.

4. The proto-device according to claim 2, wherein the microfibers are electrospun, and cross-linked.

5. The proto-device according to claim 1, wherein the microfibers are additionally attached adhesively to each other.

6. The proto-device according to claim 1, wherein the rigid matrix comprises at least one of the group consisting of a low molecular carbohydrate, comprised of monosaccharide or disaccharide, proteinaceous material and gelatin.

7. The proto-device according to claim 1, wherein the rigid matrix is disposed at least about rotationally symmetrically in respect of a longitudinal axis of the microelectrode.

8. The proto-device according to claim 1, further comprising a glidant layer disposed on the outer face of the rigid matrix.

9. The proto-device according to claim 8, wherein the glidant layer is capable of delaying access of aqueous body fluid to the rigid matrix during implantation.

10. The proto-device according to claim 1, wherein a diameter of the core or a combination of the core and the insulating layers is at most 100 μm.

11. The proto-device according to claim 1, wherein the diameter of the core or combination of the core and the insulating layer(s) varies in a distal-proximal direction.

12. The proto-device of claim 1, wherein the core comprises a metal or comprises a metal, or a noble metal comprising gold, platinum, or iridium and their alloys.

13. The proto-device of claim 1, wherein the core is comprised of at least one of an electrically conducting polymer, an electrically conducting carbon, graphite or graphene.

14. The proto-device of claim 10, wherein the insulating layer comprises a polymer material selected from the group consisting of Parylene, polyurethane and silicone.

15. The proto-device of claim 1, wherein the core is extendable in an axial direction.

16. A method for implantation of the proto-device of claim 1, wherein the proto-device has a distal end, the method comprising
inserting, with the distal end foremost, the microelectrode into soft tissue or into a pre-formed channel in the soft tissue, the channel being filled with an aqueous gel; and
controlling the position of the inserted microelectrode during a period of time extending from insertion of the microelectrode until disposition of the microfibers between the tissue and the insulating layer and/or the core of the microelectrode in a manner so as to make the microfibers form a layer abutting the tissue and the insulating layer and/or the core of the microelectrode.

17. The method for implantation of the proto-device according to claim 16, further comprising decreasing the rate of insertion with the implantation depth.

18. A method of manufacture of the proto-device of claim 1, comprising providing the proto-device; adhesively attaching biocompatible microfibers to the insulating layer and/or the core of the microelectrode and to each other; immersing a combination of the proto-device and the microfibers into an aqueous solution of a biodegradable proteinaceous or carbohydrate material; drying the combination; and optionally covering an outer face of the combination with a material selected for preventing premature dissolution of the rigid matrix during insertion thereof into soft tissue.

19. A method of manufacture of the proto-device of claim 18, wherein the material selected for the preventing of premature dissolution of the rigid matrix during insertion comprises wax or a triglyceride melting slightly above body temperature.

20. The proto-device of claim 1, wherein the proto-device is a proto-electrical lead.

* * * * *